United States Patent
Lamberty et al.

(10) Patent No.: US 7,488,741 B2
(45) Date of Patent: Feb. 10, 2009

(54) 4-AMINOPIPERIDINE DERIVATIVES, PROCESSES FOR THEIR PREPARATION AND THEIR USE AS MEDICAMENTS

(75) Inventors: Yves Lamberty, Braine-le-Château (BE); Christophe Genicot, Court-Saint-Etienne (BE)

(73) Assignee: UCB Pharma, S.A., Brussels (BE)

( * ) Notice: Subject to any disclaimer, the term of this patent is extended or adjusted under 35 U.S.C. 154(b) by 514 days.

(21) Appl. No.: 10/528,924

(22) PCT Filed: Sep. 30, 2003

(86) PCT No.: PCT/EP03/10824

§ 371 (c)(1),
(2), (4) Date: Oct. 3, 2005

(87) PCT Pub. No.: WO2004/030668

PCT Pub. Date: Apr. 15, 2004

(65) Prior Publication Data

US 2006/0128753 A1 Jun. 15, 2006

(30) Foreign Application Priority Data

Oct. 4, 2002 (EP) .................................. 02022191

(51) Int. Cl.
*A61K 31/4468* (2006.01)
*C07D 211/58* (2006.01)
(52) U.S. Cl. ...................... 514/329; 546/223; 546/227
(58) Field of Classification Search ................ 514/329; 546/223, 227
See application file for complete search history.

(56) References Cited

U.S. PATENT DOCUMENTS 4,126,689 A * 11/1978 Sanczuk et al. ............. 514/329

* cited by examiner

*Primary Examiner*—Charanjit S Aulakh
(74) *Attorney, Agent, or Firm*—McDonnell Boehnen Hulbert & Berghoff LLP

(57) ABSTRACT

4-Aminopiperidine derivatives, pharmaceutical compositions containing the same, and methods for their preparation are provided herein for the treatment of disorders of the central and/or peripheral nervous systems. In particular, the potent antidepressant activity shown by the disclosed 4-aminopiperidine derivatives are particularly useful for the prevention and/or the treatment of depression, severe depression with anxiety, anxiety disorders and affective disorders.

10 Claims, No Drawings

4-AMINOPIPERIDINE DERIVATIVES, PROCESSES FOR THEIR PREPARATION AND THEIR USE AS MEDICAMENTS

The present invention relates to 4-aminopiperidine derivatives, to processes for their preparation, to their use in therapy and to pharmaceutical compositions containing them. More particularly these compounds are useful for treatment of disorders of the central and/or peripheral nervous system. Of particular interest is the potent antidepressant activity shown by these compounds.

Therefore, these 4-aminopiperidine derivatives are particularly useful for the prevention and/or the treatment of depression, severe depression with anxiety, anxiety disorders and affective disorders.

Depression is reported to affect up to 10% of the population, with a lifetime prevalence of 19% and is linked with a significant mortality. The traditional treatment approach of depression with tricyclic antidepressants has experienced a decreased popularity since the introduction of drugs that specifically targeted the brain serotonin system, namely specific serotonin reuptake inhibitors (SSRIs) represented by the widely used fluoxetine. If it is true that SSRIs have improved side effects compared to tricyclics, data is accumulating showing that this category of drugs insufficiently covers the symptoms of anxiety and insomnia which are an inherent part of depression. Moreover, these substances may, by themselves, induce nervousness, insomnia and anxiety. Thus a substantial number of patients require co-administration of anxiolytic/hypnotic medication such as benzodiazepines or antihistamines. The latter compounds, particularly hydroxyzine, might be more suited than benzodiazepines in co-administration with SSRIs. Another important side effect of SSRIs is sexual dysfunction that seems to be mediated by serotonin 5-HT2 receptors.

Therefore, to avoid polytherapy, one chemical entity that possesses the efficacy of SSRIs and have added properties that could relieve nervousness, anxiety and sexual dysfunction could be of a high benefit to the patient. In particular, such a molecule should have important affinities towards serotonin reuptake sites (main mode of action of SSRIs); histamine H1 receptors to improve nervousness, anxiety and facilitate sleep; and serotonin 5-HM2 receptors, the blockade of which is expected to prevent sexual side effects.

Our research efforts in this field have led us to discover molecules possessing these 3 properties, i.e inhibition of serotonin reuptake sites, blockade of histaminergic H1 receptors and blockade of serotonin 5-HT2 receptors.

Recent pharmacological studies conducted by the applicant have revealed unrecognised and potent pharmacological properties of the herein mentioned novel 4-aminopiperidine derivatives of formula (I), which suggest that they may be useful in treating disorders such as those mentioned above, but not limited to them.

U.S. Pat. No. 5,461,066 describes 4-aminopiperidine derivatives as synthesis intermediates. The abstract of the Japanese patent application JP 05148234 describes the two following compounds, N-[(4-chlorophenyl)methyl]-N-phenyl-4-piperidinamine, N-phenyl-N-(phenylmethyl)-4-piperidinamine, as having antihistaminic and anti-allergic activity.

According to one aspect therefore, the present invention provides 4-aminopiperidine derivatives of formula I, including pharmaceutically acceptable salts thereof,

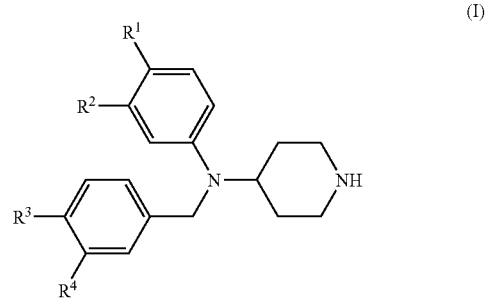

(I)

wherein $R^1$, $R^2$, $R^3$, $R^4$ independently are selected from hydrogen, fluorine, chlorine, methyl and trifluoromethyl, with the proviso that, if $R^1$, $R^2$ and $R^4$ are hydrogen, then $R^3$ is not hydrogen or halogen.

Preferred compounds according to the invention are compounds of formula I wherein:
$R^2$ is hydrogen, fluorine or methyl,
$R^4$ is hydrogen, fluorine, chlorine or trifluoromethyl,
$R^1$ and $R^3$ having the same definitions as described above, with the proviso that, if $R^1$, $R^2$ and $R^4$ are hydrogen, then $R^3$ is not hydrogen or halogen, or a pharmaceutically acceptable salt thereof.

More preferred compounds according to the invention are compounds of formula I wherein:
$R^1$ is hydrogen, fluorine or chlorine,
$R^2$ is hydrogen, fluorine or methyl,
$R^3$ is hydrogen, fluorine, chlorine or methyl,
$R^4$ is hydrogen, fluorine or chlorine.
with the proviso that, if $R^1$, $R^2$ and $R^4$ are hydrogen, then $R^3$ is not hydrogen or halogen, or a pharmaceutically acceptable salt thereof.

Most preferred compounds according to the invention are compounds of formula I wherein:
$R^1$ is hydrogen or fluorine,
$R^2$ is hydrogen or fluorine,
$R^3$ is fluorine or methyl,
$R^4$ is hydrogen,
with the proviso that, if $R^1$, $R^2$ and $R^4$ are hydrogen, then $R^3$ is not fluorine, or a pharmaceutically acceptable salt thereof.

Preferred compounds of the invention are:
N-phenyl-N-[3-(trifluoromethyl)benzyl]-4-piperidinamine; N-(3-chlorobenzyl)-N-phenyl-4-piperidinamine; N-(3,4-difluorobenzyl)-N-phenyl-4-piperidinamine; N-(3,4-dichlorobenzyl)-N-phenyl-4-piperidinamine; N-(4-methylbenzyl)-N-phenyl-4-piperidinamine; N-phenyl-N-[4-(trifluoromethyl)benzyl]-4-piperidinamine; N-(3-chlorobenzyl)-N-(3-fluorophenyl)-4-piperidinamine; N-(3,4-difluorobenzyl)-N-(3-fluorophenyl)-4-piperidinamine; N-(4-fluorobenzyl)-N-(3-fluorophenyl)-4-piperidinamine; N-(4-chlorobenzyl)-N-(3-fluorophenyl)-4-piperidinamine; N-(3,4-dichlorobenzyl)-N-(3-fluorophenyl)-4-piperidinamine; N-(3-fluorophenyl)-N-(4-methylbenzyl)-4-piperidinamine; N-(3-fluorophenyl)-N-[4-(trifluoromethyl)benzyl]-4-piperidinamine; N-(3-chlorobenzyl)-N-(3-methylphenyl)-4-piperidinamine; N-(3,4-difluorobenzyl)-N-(3-methylphenyl)-4-piperidinamine; N-(4-fluorobenzyl)-N-(3-methylphenyl)-4-piperidinamine; N-(4-chlorobenzyl)-N-(3-methylphenyl)-4-piperidinamine; N-(3,4-dichlorobenzyl)-N-(3- methylphenyl)-4-piperidinamine; N-(3-methylphenyl)-N-[4-(trifluoromethyl)benzyl]-4-piperidinamine; N-benzyl-N-(4-fluorophenyl)-4-piperidinamine; N-(4-fluorophenyl)-N-[3-(trifluoromethyl)benzyl]-4-piperidinamine; N-(3-chlorobenzyl)-N-(4-fluorophenyl)-4-piperidinamine; N-(3,4-difluorobenzyl)-N-(4-fluorophenyl)-4-piperidinamine; N-(4-fluorobenzyl)-N-(4-fluorophenyl)-4-piperidinamine; N-(4-chlorobenzyl)-N-(4-fluorophenyl)-4-piperidinamine; N-(3,4-dichlorobenzyl)-N-(4-fluorophenyl)-4-piperidinamine; N-(4-fluorophenyl)-N-(4-methylbenzyl)-4-piperidinamine; N-(4-fluorophenyl)-N-[4-(trifluoromethyl)benzyl]-4-piperidinamine; N-(4-chlorophenyl)-N-(4-fluorobenzyl)-4-piperidinamine; N-(3-chlorobenzyl)-N-(4-methylphenyl)-4-piperidinamine; N-(3,4-difluorobenzyl)-N-(4-methylphenyl)-4-piperidinamine; N-(4-fluorobenzyl)-N-(4-methylphenyl)-4-piperidinamine; N-(4-chlorobenzyl)-N-(4-methylphenyl)-4-piperidinamine; N-(3,4-dichlorobenzyl)-N-(4-methylphenyl)-4-piperidinamine; N-(4-methylphenyl)-N-[4-(trifluoromethyl)benzyl]-4-piperidinamine; N-(4-fluorobenzyl)-N-[4-(trifluoromethyl)phenyl]-4-piperidinamine or pharmaceutically acceptable salts thereof.

More preferred compounds of the invention are:
N-(3-chlorobenzyl)-N-phenyl-4-piperidinamine; N-(3,4-difluorobenzyl)-N-phenyl-4-piperidinamine; N-(4-methylbenzyl)-N-phenyl-4-piperidinamine; N-(3-chlorobenzyl)-N-(3-chlorophenyl)-4-piperidinamine; N-(3,4-difluorobenzyl)-N-(3-fluorophenyl)-4-piperidinamine; N-(4-fluorobenzyl)-N-(3-fluorophenyl)-4-piperidinamine; N-(4-chlorobenzyl)-N-(3-fluorophenyl)-4-piperidinamine; N-(3-fluorophenyl)-N-(4-methylbenzyl)-4-piperidinamine; N-(4-fluorobenzyl)-N-(3-methylphenyl)-4-piperidinamine; N-benzyl-N-(4-fluorophenyl)-4-piperidinamine; N-(3,4-difluorobenzyl)-N-(4-fluorophenyl)-4-piperidinamine; N-(4-fluorobenzyl)-N-(4-fluorophenyl)-4-piperidinamine; N-(4-chlorobenzyl)-N-(4-fluorophenyl)-4-piperidinamine; N-(4-fluorophenyl)-N-(4-methylbenzyl)-4-piperidinamine; N-(4-chlorophenyl)-N-(4-fluorobenzyl)-4-piperidinamine or pharmaceutically acceptable salts thereof.

Most preferred compounds of the invention are:
N-(4-methylbenzyl)-N-phenyl-4-piperidinamine; N-(4-fluorobenzyl)-N-(3-fluorophenyl)-4-piperidinamine; N-(3-fluorophenyl)-N-(4-methylbenzyl)-4-piperidinamine; N-(4-fluorobenzyl)-N-(4-fluorophenyl)-4-piperidinamine; N-(4-fluorophenyl)-N-(4-methylbenzyl)-4-piperidinamine or pharmaceutically acceptable salts thereof.

The best results have been obtained with N-(4-fluorobenzyl)-N-(3-fluorophenyl)-4-piperidinamine and N-(3-fluorophenyl)-N-(4-methylbenzyl)-4-piperidinamine, or pharmaceutically acceptable salts thereof.

The "pharmaceutically acceptable salts" according to the invention include therapeutically active, non-toxic acid salt forms which the compounds of formula I are able to form. The acid addition salt form of a compound of formula I that occurs in its free form as a base can be obtained by treating the free base with an appropriate acid such as an inorganic acid, for example, a hydrohalic such as hydrochloric or hydrobromic, sulfuric, nitric, phosphoric and the like; or an organic acid, such as, for example, acetic, hydroxyacetic, propanoic, lactic, pyruvic, malonic, succinic, maleic, fumaric, malic, tartaric, citric, methanesulfonic, ethanesulfonic, benzenesulfonic, p-toluenesulfonic, cyclamic, salicylic, p-aminosalicylic, pamoic and the like.

Conversely said salt forms can be converted into the free forms by treatment with an appropriate base.

Compounds of the formula I and their salts can be in the form of a solvate, which is included within the scope of the present invention. Such solvates include for example hydrates, alcoholates and the like.

The present invention concerns also processes for preparing the compounds of formula I.

The compounds of formula I according to the invention can be prepared analogously to conventional methods as understood by the person skilled in the art of synthetic organic chemistry.

The following process description sets forth certain synthesis routes in an illustrative manner. Other alternative and/or analogous methods will be readily apparent to those skilled in this art.

According to one embodiment, compounds having the general formula I may be prepared by the protection of a compound of formula II according to the equation:

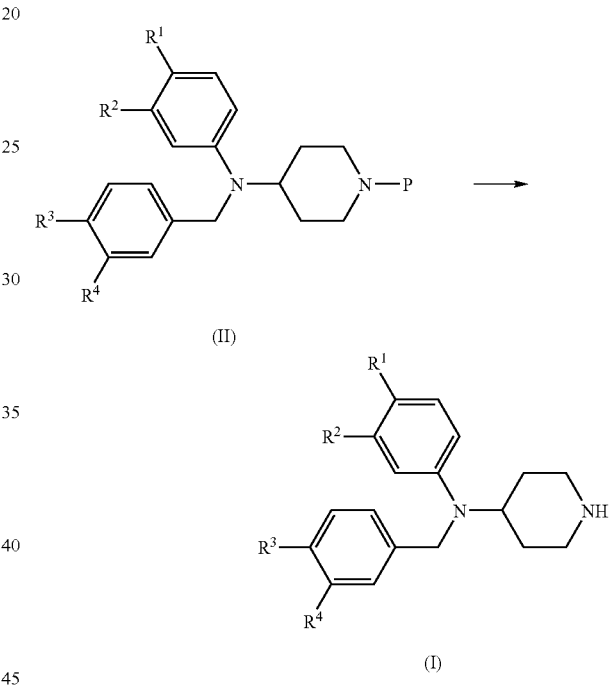

wherein P is a protecting group, $R^1$, $R^2$, $R^3$ and $R^4$ having the same definitions as described above.

The protecting group P may be any suitable amine protecting group such as, for example, carbamate, sulfenyl derivatives, sulfonyl derivatives, alkyl and aryl. Non-limiting examples are methoxycarbonyl, ethoxycarbonyl, tert-butoxycarbonyl (Boc), 9-fluorenylmethoxycarbonyl (Fmoc), 9-(2-sulfo)fluorenylmethoxycarbonyl, 9-(2,7-dibromo)fluorenylmethoxycarbonyl, 2,2,2-trichloroethoxycarbonyl (Troc), 2-phenylethoxycarbonyl, 2-chloroethoxycarbonyl, benzyloxycarbonyl, p-methoxybenzyloxycarbonyl, benzenesulfenyl, 2-nitrobenzenesulfenyl, tosyl, benzenesulfonyl, methyl, tert-butyl, allyl, benzyl, bis(4-methoxyphenyl)methyl or 2,4-dinitrophenyl. For more details concerning deprotection methods, see "Protective Groups in Organic Chemistry", Chapter 2, J. F. W. Omie, Plenum Press, London and New York, 1973 and "Protective Groups in Organic Synthesis", Chapter 7, Th. W. Greene, John Wiley & Sons, 1999.

This transformation may be carried out according to any procedure known to the person skilled in the art.

Compounds of formula II may be prepared by reaction of a compound of formula III with a compound of formula IV according to the equation

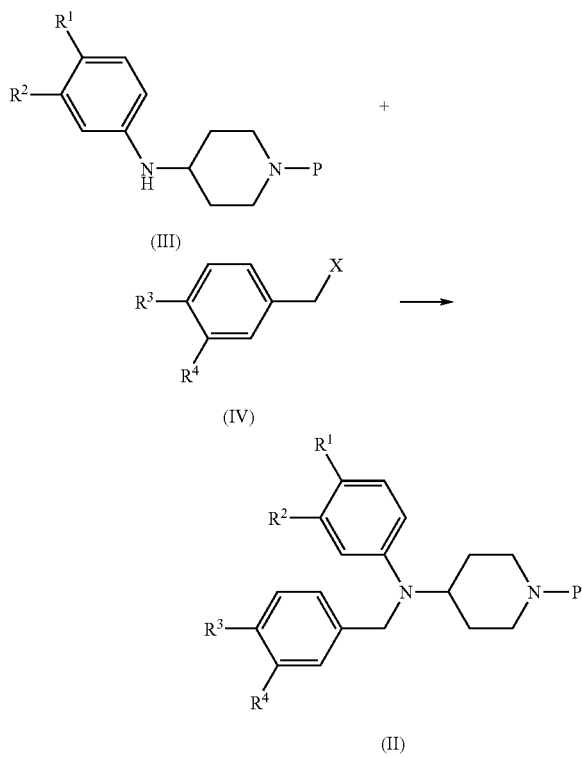

wherein X is an halogen atom, preferably bromine, P, $R^1$, $R^2$, $R^3$ and $R^4$ having the same definitions as described above.

This transformation may be carried out in an inert solvent, for example acetonitrile or dimethylformamide, in the presence of an organic or an inorganic base, for example triethylamine or potassium carbonate, between 50 and 100° C.

Compounds of formula IV are commercially available.

Compounds of formula III may be prepared by reaction of a compound of formula V with a ketone of formula VI according to the equation

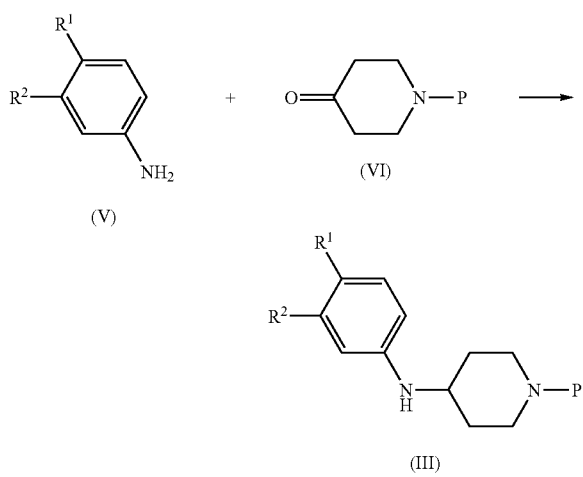

This transformation may be carried out in an alcoholic solvent, for example methanol, in the presence of 1 to 2 equivalents of an acid, for example acetic acid, and in the presence of 1 to 2 equivalents of a reductive agent such as sodium cyanoborohydride.

Compounds of formula V and compounds of formula VI are commercially available.

In another aspect, the invention provides 4-aminopiperidine derivatives of formula (I) including the pharmaceutically acceptable salts thereof for their use as medicament.

It has finally been found that compounds of formula (I) and the pharmaceutically acceptable salts thereof are particularly effective antidepressant agents.

Therefore, these compounds are particularly useful for the prevention and/or the treatment of depression and severe depression with anxiety.

These compounds may also be used for the prevention and/or the treatment of other neurological disorders including anxiety disorders, particularly generalized anxiety disorder (GAD), panic disorder (PD), post traumatic stress disorder (PTSD), social anxiety disorder (SAD), obsessive compulsive disorder and agoraphobia, bipolar disorders, mania, chronic pain, neuropathic pain, migraine, cerebral ischemia, cardiac arrhythmia, myotonia, cocaine and alcohol abuse, stroke, myoclonus, tremor, neonatal cerebral haemorrage, amyotrophic lateral sclerosis (ALS), spasticity, Parkinson's disease, and other neurodegenerative and movement disorders.

Thus, the present invention in a further aspect concerns the use of compounds of formula (I) or the pharmaceutically acceptable salts thereof as defined above, for the manufacture of a medicament for the treatment and/or prophylaxis of neurological disorders such as mentioned above.

In particular, the present invention concerns the use of compounds of formula (I) and the pharmaceutically acceptable salts thereof as defined above, for the manufacture of a medicament for the treatment and/or prophylaxis of depression.

The present invention also concerns a method for treating depression, in a mammal in need of such treatment, comprising administering a therapeutic dose of at least one compound of formula (I) and the pharmaceutically acceptable salts thereof to a patient.

The methods of the invention comprise administration to a mammal (preferably human) suffering from above mentioned diseases of a pharmaceutical composition according to the invention in an amount sufficient to alleviate the condition. The compound is conveniently administered in any suitable unit dosage form, including but not limited to one containing 0.5 to 500 mg, preferably 1 to 100 mg of active ingredient per unit dosage form.

The term "treatment" as used by the Applicant means curative treatment and prophylactic treatment.

By "curative" we mean the efficaciousness of formula (I) in treating the current episode of depressive phase.

By "prophylactic" or "maintenance" we mean the prevention of the recurrence of depressive episodes.

For treating diseases, compounds of formula (I) or their pharmaceutically acceptable salts may be employed at an effective daily dosage and administered via a pharmaceutical composition.

Therefore, another embodiment of the present invention is a pharmaceutical composition that includes an effective amount of a compound of formula (I) or its pharmaceutically acceptable salts or a derivative in combination with a pharmaceutically acceptable carrier for any of the disorders described herein.

To prepare the pharmaceutical composition of this invention, one or more of the compounds of formula (I), or their pharmaceutically acceptable salts, are intimately admixed with a pharmaceutical carrier according to conventional pharmaceutical compounding techniques, which carrier may take a wide variety of forms depending on the form of preparation desired for administrating, e.g., oral, rectal, or parenteral.

The present invention requires administration of an effective dose of the compounds for the treatment and/or the prophylaxis of diseases. The dose required in accordance with the invention should be sufficiently high to permit the relief of diseases. Pharmaceutical compositions comprising compounds can, for example, be administered orally or parenterally, i.e., intravenously, intramuscularly or subcutaneously, intrathecally.

Pharmaceutical compositions which can be used for oral administration can be solids or liquids and can, for example, be in the form of tablets, pills, dragees, gelatin capsules, solutions, syrups, and the like.

To this end, compounds can be used mixed with an inert diluent or a non-toxic pharmaceutically acceptable vehicle such as starch or lactose, for example. Optionally, these pharmaceutical compositions can also contain a binder such as microcrystalline cellulose, gum tragacanth or gelatine, a disintegrant such as alginic acid, a lubricant such as magnesium stearate, a glidant such as colloidal silicon dioxide, a sweetener such as sucrose or saccharin, or colouring agents or a flavouring agent such as peppermint or methyl salicylate.

They also comprise compositions which can release the active substance in a controlled manner. Pharmaceutical compositions which can be used for parenteral administration are in the pharmaceutical forms which are known for this mode of administration and are in the form of aqueous or oily solutions or suspensions generally contained in ampoules, disposable syringes, glass or plastics vials or infusion containers.

In addition to the active compound, these solutions or suspensions can optionally also contain a sterile diluent such as water for injection, a physiological saline solution, oils, polyethylene glycols, glycerine, propylene glycol or other synthetic solvents, antibacterial agents such as benzyl alcohol, antioxidants such as ascorbic acid or sodium bisulphite, chelating agents such as ethylene diamine-tetra-acetic acid, buffers such as acetates, citrates or phosphates and agents for adjusting the osmolarity, such as sodium chloride or dextrose.

These pharmaceutical forms are prepared using methods which are routinely used by pharmacists.

The percentage of compound of formula (I) in the pharmaceutical compositions can fall within a wide range of concentrations and depends on a variety of factors such as the patient's sex, age, weight and medical condition, as well as on the method of administration. Thus the quantity of compound of formula (I) in compositions for oral administration is at least 0.5% by weight and can be up to 80% by weight with respect to the composition weight, etc.).

In another embodiment, the present invention concerns also the synthesis intermediates of formula II, or III, wherein the substituents R and the protecting group P are defined as above.

The preferred compounds of formula II are tert-butyl 4-[3-fluoro(4-fluorobenzyl)anilino]-1-piperidinecarboxylate; tert-butyl 4-{[3-(trifluoromethyl)benzyl]anilino}-1-piperidinecarboxylate; tert-butyl 4-[(3-chlorobenzyl)anilino]-1-piperidinecarboxylate; tert-butyl 4-[(3,4-difluorobenzyl)anilino]-1-piperidinecarboxylate; tert-butyl 4-[(3,4-dichlorobenzyl)anilino]-1-piperidinecarboxylate; tert-butyl 4-[(4-methylbenzyl)anilino]-1-piperidinecarboxylate; tert-butyl 4-{[4-(trifluoromethyl)benzyl]anilino}-1-piperidinecarboxylate; tert-butyl 4-[(3,4-difluorobenzyl)-3-fluoroanilino]-1-piperidinecarboxylate; tert-butyl 4-[(4-chlorobenzyl)-3-fluoroanilino]-1piperidinecarboxylate; tert-butyl 4-[(3,4-dichlorobenzyl)-3-fluoroanilino]-1piperidinecarboxylate; tert-butyl 4-[3-fluoro(4-methylbenzyl)anilino-1-piperidinecarboxylate; tert-butyl 4-(3-fluoro[4-(trifluoromethyl)benzyl) anilino]-1-piperidinecarboxylate; tert-butyl 4-[(3-chlorobenzyl)-3-methylanilino]-1-piperidinecarboxylate; tert-butyl 4-[(3,4-difluorobenzyl)-3-methylanilino]-1-piperidinecarboxylate; tert-butyl 4-[(4-fluorobenzyl)-3-methylanilino]-1-piperidinecarboxylate; tert-butyl 4-[(4-chlorobenzyl)-3-methylanilino]-1-piperidinecarboxylate; tert-butyl 4-[(3,4-dichlorobenzyl)-3-methylanilino]-1-piperidinecarboxylate; tert-butyl 4-{3-methyl[4-(trifluoromethyl)benzyl]anilino}-1-piperidinecarboxylate; tert-butyl 4-(benzyl-4-fluoroanilino)-1-piperidinecarboxylate; tert-butyl 4-{4-fluoro[3-(trifluoromethyl)benzyl]anilino}-1-piperidinecarboxylate; tert-butyl 4-[(3-chlorobenzyl)-4-fluoroanilino]-1-piperidinecarboxylate; tert-butyl 4-[(3,4-difluorobenzyl)-4-fluoroanilino]-1-piperidinecarboxylate; tert-butyl 4-[4-fluoro(4-fluorobenzyl)anilino]-1-piperidinecarboxylate; tert-butyl 4-[(4-chlorobenzyl)-4-fluoroanilino]-1piperidinecarboxylate; tert-butyl 4-[(3,4-dichlorobenzyl)-4-fluoroanilino]-1piperidinecarboxylate; tert-butyl 4-[4-fluoro(4-methylbenzyl)anilino]-1-piperidinecarboxylate; tert-butyl 4-{4-fluoro[4-(trifluoromethyl)benzyl]anilino}-1-piperidinecarboxylate; tert-butyl 4-[4-chloro(4-fluorobenzyl)anilino]-1-piperidinecarboxylate; tert-butyl 4-[(3-chlorobenzyl)-4-methylanilino]-1-piperidinecarboxylate; tert-butyl 4-[(3,4-difluorobenzyl)-4-methylanilino]-1-piperidinecarboxylate; tert-butyl 4-[(4-fluorobenzyl)-4-methylanilino]-1-piperidinecarboxylate; tert-butyl 4-[(4-chlorobenzyl)-4-methylanilino]-1-piperidinecarboxylate; tert-butyl 4-[(3,4-dichlorobenzyl)-4-methylanilino]-1-piperidinecarboxylate; tert-butyl 4-{4-methyl[4-(trifluoromethyl)benzyl]anilino}-1-piperidinecarboxylate; tert-butyl 4-[(4-fluorobenzyl)-4-(trifluoromethyl)anilino]-1-piperidinecarboxylate and tert-butyl 4-[(3-chlorobenzyl)-3-fluoroanilino]-1-piperidinecarboxylate.

The preferred compounds of formula III are tert-butyl 4-(3-fluoroanilino)-1-piperidinecarboxylate; tert-butyl 4-(3-toluidino)-1-piperidinecarboxylate; tert-butyl 4-(4-toluidino)-1-piperidinecarboxylate.

The following examples are provided for illustrative purposes only and are not intended, nor should they be construed, as limiting the invention in any manner. Those skilled in the art will appreciate that routine variations and modifications of the following examples can be made without exceeding the spirit or scope of the invention.

Unless otherwise specified in the examples, characterisation of the compounds was performed according to the following methods:

NMR spectra are recorded on a BRUKER AC 250 Fourier Transform NMR Spectrometer fitted with an Aspect 3000 computer and a 5 mm $^1H/^{13}C$ dual probe head or BRUKER DRX 400 FT NMR fitted with a SG Indigo$^2$ computer and a 5 mm inverse geometry $^1H/^{13}C/^{15}N$ triple probe head. The compound is studied in DMSO-$d_6$ (or CDCl$_3$) solution at a probe temperature of 313 K and at concentrations ranging from 2 to 20 mg/ml. The instrument is locked on the deuterium signal of DMSO-$d_6$ (or CDCl$_3$). Chemical shifts are given in ppm downfield from TMS taken as internal standard. DMSO-$d_6$ (deuterated dimethyl sulfoxide).

Mass spectrometric measurements in LC/MS mode are performed as follows:

HPLC Conditions

Analyses are performed using a WATERS Alliance HPLC system mounted with an INERTSIL ODS 3-, DP 5 μm, 250× 4.6 mm column.

The gradient runs from 100% solvent A (acetonitrile, water, TFA (10/90/0.1, v/v/v)) to 100% solvent B (acetonitrile, water, TFA (90/10/0.1, v/v/v)) in 7 min with a hold at 100% B of 4 min. The flow rate is set at 2.5 ml/min and a split of 1/10 is used just before API source. The chromatography is carried out at 30° C.

MS Conditions

Samples are dissolved in acetonitrile/water, 70/30, v/v at the concentration of about 250 μg/ml. API spectra (+ or −) are performed using a FINNIGAN (San Jose, Calif., USA) LCQ ion trap mass spectrometer. APCI source operates at 450° C. and the capillary heater at 160° C. ESI source operates at 3.5 kV and the capillary heater at 210° C.

Mass spectrometric measurements in EI/DIP mode are performed as follows: samples are vaporized by heating the probe from 50° C. to 250° C. in 5 min. EI (Electron Impact) spectra are recorded using a FINNIGAN (San Jose, Calif., USA) TSQ 700 tandem quadrupole mass spectrometer. The source temperature is set at 150° C.

Mass spectrometric measurements on a TSQ 700 tandem quadrupole mass spectrometer (Finnigan MAT, San Jose, Calif., USA) in GC/MS mode are performed with a gas chromatograph model 3400 (Varian, Walnut Creek, Calif., USA) fitted with a split/splitless injector and a DB-5MS fused-silica column (15 m×0.25 mm I.D., 1 μm) from J&W Scientific (Folsom, Calif., USA). Helium (purity 99.999%) is used as carrier gas. The injector (CTC A200S autosampler) and the transfer line operate at 290 and 250° C., respectively. Sample (1 μl) is injected in splitless mode and the oven temperature is programmed as follows: 50° C. for 5 min., increasing to 280° C. (23° C./min) and holding for 10 min. The TSQ 700 spectrometer operates in electron impact (En or chemical ionization (CI/CH4) mode (mass range 33-800, scan time 1.00 sec). The source temperature is set at 150° C.

Water content is determined using a Metrohm microcoulometric Karl Fischer titrator.

Preparative chromatographic separations are performed on silicagel 60 Merck, particle size 15-40 μm, reference 1.15111.9025, using in-house modified Jobin Yvon-type axial compression columns (80 mm i.d.), flow rates between 70 and 150 ml/min. Amount of silicagel and solvent mires are as described in individual procedures.

Melting points are determined on a Büchi 535 Totoli-type fusionometre, and are not corrected, or by the onset temperature on a Perkin Elmer DSC 7.

Unless specified otherwise in the examples, the compounds are obtained in the neutral form.

EXAMPLE 1

Synthesis of Compounds of Formula I

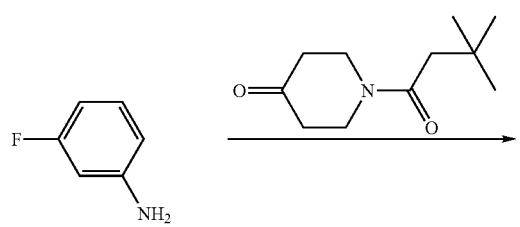

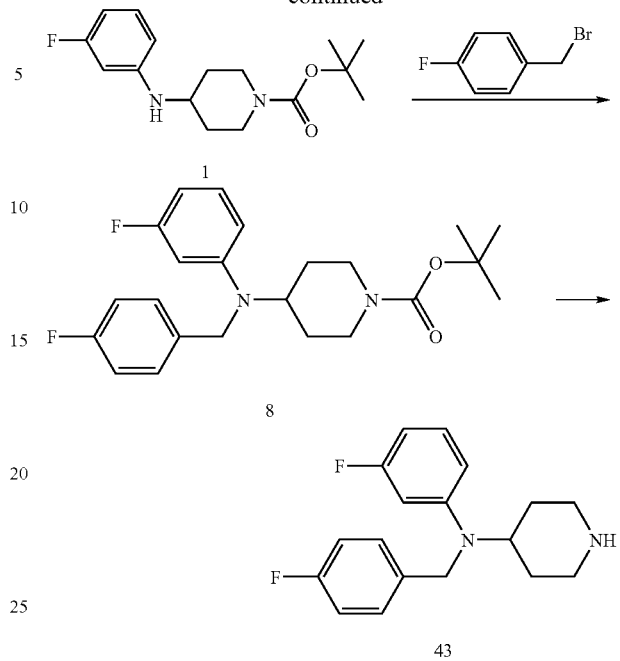

1.1 Synthesis of tert-butyl 4-(3-fluoroanilino)-1-piperidinecarboxylate 1

3-fluoroaniline (40 g) was dissolved in MeOH and the solution was cooled to 0° C. Tert-butyl 4-oxo-1-piperidinecarboxylate (79 g, 1.1 eq), acetic acid (26.8 ml, 1.3 eq) and sodium cyanoborohydride (29 g, 1.3 eq, portionwise) were added successively to the solution. The reaction mixture was stirred at room temperature until completion. The reaction mixture was then cooled to 0° C. and an aqueous solution of NaOH (20%) was poured into the mixture (pH~10). The precipitate was filtered off, washed with water, dried and recrystallised from iPrOH to give tert-butyl 4-(3-fluoroanilino)-1-piperidinecarboxylate 1 (68.5 g).

Yield: 63%.

MS (MH+): 295.

Compounds of formula m listed in table 1 can be synthesized in an analogous way.

TABLE 1 compounds of formula III.

| n° | IUPAC Name | MH+ (LC – MS) |
|---|---|---|
| 1 | tert-butyl 4-(3-fluoroanilino)-1-piperidinecarboxylate | 295 |
| 2 | tert-butyl 4-anilino-1-piperidinecarboxylate | 277 |
| 4 | tert-butyl 4-(4-fluoroanilino)-1-piperidinecarboxylate | 295 |
| 5 | tert-butyl 4-(4-chloroanilino)-1-piperidinecarboxylate | 311-313 |
| 7 | tert-butyl 4-[4-(trifluoromethyl)anilino]-1-piperidinecarboxylate | 344 (MH·+, GC – MS) |

1.2 Synthesis of tert-butyl 4-[3-fluoro(4-fluorobenzyl)anilino]-1-piperidinecarboxylate 8

Tert-butyl 4-(3-fluoroanilino)-1-piperidinecarboxylate 1 (20 g) was dissolved in acetonitrile (250 ml). Potassium carbonate (33.2 g) and 1-(bromomethyl)-4-fluorobenzene (11 ml) were added to the solution. The reaction mixture was heated at reflux overnight, then cooled, concentrated and the residue was taken up in dichloromethane and water. The aqueous layer was washed twice with dichloromethane. The combined organic layers were dried over MgSO$_4$ and concentrated. The resulting white solid was triturated in hexane and filtered off to afford tert-butyl 4-[3-fluoro(4-fluorobenzyl) anilino]-1-piperidinecarboxylate 8 (25.5 g).

Yield: 89%.

MS (MH$^+$): 403

Compounds of formula II listed in table 2 can be synthesized in an analogous way.

TABLE II compounds of formula II.

| n° | IUPAC Name | MH$^+$ (LC/MS) |
|---|---|---|
| 8 | tert-butyl 4-[3-fluoro(4-fluorobenzyl)anilino]-1-piperidinecarboxylate | 403 |
| 10 | tert-butyl 4-[(3-chlorobenzyl)anilino]-1-piperidinecarboxylate | 401/403 |
| 11 | tert-butyl 4-[(3,4-difluorobenzyl)anilino]-1-piperidinecarboxylate | 403 |
| 13 | tert-butyl 4-[(4-methylbenzyl)anilino]-1-piperidinecarboxylate | 381 |
| 14 | tert-butyl 4-{[4-(trifluoromethyl)benzyl]anilino}1-piperidinecarboxylate | 435 |
| 15 | tert-butyl 4-[(3,4-difluorobenzyl)-3-fluoroanilino]-1-piperidinecarboxylate | 421 |
| 16 | tert-butyl 4-[(4-chlorobenzyl)-3-fluoroanilino]-1-piperidinecarboxylate | 419/421 |
| 18 | tert-butyl 4-[3-fluoro(4-methylbenzyl)anilino]-1-piperidinecarboxylate | 399 |
| 26 | tert-butyl 4-(benzyl-4-fluoroanilino)-1-piperidinecarboxylate | 385 |
| 28 | tert-butyl 4-[(3-chlorobenzyl)-4-fluoroanilino]-1-piperidinecarboxylate | 419/421 |
| 29 | tert-butyl 4-[(3,4-difluorobenzyl)-4-fluoroanilino]-1-piperidinecarboxylate | 421 |
| 30 | tert-butyl 4-[4-fluoro(4-fluorobenzyl)anilino]-1-piperidinecarboxylate | 403 |

TABLE II-continued compounds of formula II.

| n° | IUPAC Name | MH$^+$ (LC/MS) |
|---|---|---|
| 31 | tert-butyl 4-[(4-chlorobenzyl)-4-fluoroanilino]-1-piperidinecarboxylate | 419/421 |
| 34 | tert-butyl 4-{4-fluoro[4-(trifluoromethyl)benzyl]anilino}-1-piperidinecarboxylate | 453 |

1.3 Synthesis of N-(4-fluorobenzyl)-N-(3-fluorophenyl)-4-piperidinamine 43

Tert-butyl 4-[3-fluoro(4-fluorobenzyl)anilino]-1-piperidinecarboxylate 8 (25.5 g) was dissolved in dichloromethane and the solution was cooled to 0° C. TFA (30 ml) was added to the solution and the reaction mixture was stirred at room temperature. After 1 h 30, TFA (20 ml) was added and the reaction mixture was stirred for a further 30 minutes. The solvent was removed under vacuum and the residue was taken up in dichloromethane and water. The aqueous phase was alkalized by addition of NaOH and washed with dichloromethane. The combined organic layers were dried over MgSO$_4$ and concentrated. The crude was purified by chromatography (eluant: CH$_2$Cl$_2$/MeOH/NH$_4$OH 95/5/0.5) to give N-(4-fluorobenzyl)-N-(3-fluorophenyl)-4-piperidinamine (18.4 g) as a free base.

A solution of ether saturated with HCl was added to N-(4-fluorobenzyl)-N-(3-fluorophenyl)-4-piperidinamine dissolved in ether. The precipitate was filtered off, washed with ether and dried in an oven (50° C.) under vacuum to afford 17.51 g of N-(4-fluorobenzyl)-N-(3-fluorophenyl)-4-piperidinamine 43 (2 HCl, 0.5 H$_2$O) as a white solid.

Yield: 72%.

MS (MH$^+$): 303

Compounds of formula I listed in table 3 can be synthesized in an analogous way.

TABLE 3 compounds of formula I.

| n° | Salt | IUPAC Name | MH$^+$(LC – MS) |
|---|---|---|---|
| 43 | 2 HCl, 0.5 H$_2$O | N-(4-fluorobenzyl)-N-(3-fluorophenyl)-4-piperidinamine | 303 |
| 44 | 2 CF$_3$COOH | N-(4-fluorobenzyl)-N-(3-fluorophenyl)-4-piperidinamine | 303 |
| 45 | 2 CF$_3$COOH | N-phenyl-N-[3-(trifluoromethyl)benzyl]-4-piperidinamine | 335 |
| 46 | 2 HCl, 0.5 H$_2$O | N-(3-chlorobenzyl)-N-phenyl-4-piperidinamine | 301 |
| 47 | 2 CF$_3$COOH | N-(3-chlorobenzyl)-N-phenyl-4-piperidinamine | 301 |
| 48 | 2 HCl, 0.5 H$_2$O | N-(3,4-difluorobenzyl)-N-phenyl-4-piperidinamine | 303 |
| 49 | 2 CF$_3$COOH | N-(3,4-difluorobenzyl)-N-phenyl-4-piperidinamine | 303 |
| 50 | 2 CF$_3$COOH | N-(3,4-dichlorobenzyl)-N-phenyl-4-piperidinamine | 335/337/339 |
| 51 | 2 HCl, 1 H$_2$O | N-(4-methylbenzyl)-N-phenyl-4-piperidinamine | 281 |
| 52 | 2 CF$_3$COOH | N-(4-methylbenzyl)-N-phenyl-4-piperidinamine | 281 |
| 53 | 2 HCl, 1 H$_2$O | N-phenyl-N-[4-(trifluoromethyl)benzyl]-4-piperidinamine | 335 |
| 54 | 2 CF$_3$COOH | N-phenyl-N-[4-(trifluoromethyl)benzyl]-4-piperidinamine | 335 |
| 55 | 2 CF$_3$COOH | N-(3-chlorobenzyl)-N-(3-fluorophenyl)-4-piperidinamine | 319/321 |
| 56 | 2 CF$_3$COOH | N-(3,4-difluorobenzyl)-N-(3-fluorophenyl)-4-piperidinamine | 321 |
| 57 | 2 HCl, 0.5 H$_2$O | N-(3,4-difluorobenzyl)-N-(3-fluorophenyl)-4-piperidinamine | 321 |
| 58 | 2 CF$_3$COOH | N-(4-chlorobenzyl)-N-(3-fluorophenyl)-4-piperidinamine | 319/321 |
| 59 | 2 CF$_3$COOH | N-(3,4-dichlorobenzyl)-N-(3-fluorophenyl)-4-piperidinamine | 353 |

TABLE 3-continued compounds of formula I.

| n° | Salt | IUPAC Name | MH+(LC – MS) |
|---|---|---|---|
| 60 | 2 HCl, 0.5 H$_2$O | N-(3-fluorophenyl)-N-(4-methylbenzyl)-4-piperidinamine | 299 |
| 61 | 2 CF$_3$COOH | N-(3-fluorophenyl)-N-[4-(trifluoromethyl)benzyl]-4-piperidinamine | 353 |
| 62 | 2 CF$_3$COOH | N-(3-chlorobenzyl)-N-(3-methylphenyl)-4-piperidinamine | 315/317 |
| 63 | 2 CF$_3$COOH | N-(3,4-difluorobenzyl)-N-(3-methylphenyl)-4-piperidinamine | 317 |
| 64 | 2 CF$_3$COOH | N-(4-fluorobenzyl)-N-(3-methylphenyl)-4-piperidinamine | 299 |
| 65 | 2 CF$_3$COOH | N-(4-chlorobenzyl)-N-(3-methylphenyl)-4-piperidinamine | 315 |
| 66 | 2 CF$_3$COOH | N-(3,4-dichlorobenzyl)-N-(3-methylphenyl)-4-piperidinamine | 349/351/353 |
| 67 | 2 CF$_3$COOH | N-(3-methylphenyl)-N-[4-(trifluoromethyl)benzyl]-4-piperidinamine | 349 |
| 68 | 2 HCl, 1 H$_2$O | N-benzyl-N-(4-fluorophenyl)-4-piperidinamine | 285 |
| 69 | 2 CF$_3$COOH | N-benzyl-N-(4-fluorophenyl)-4-piperidinamine | 285 |
| 70 | 2 CF$_3$COOH | N-(4-fluorophenyl)-N-[3-(trifluoromethyl)benzyl]-4-piperidinamine | 353 |
| 71 | 2 HCl, 0.5 H$_2$O | N-(3-chlorobenzyl)-N-(4-fluorophenyl)-4-piperidinamine | 319 |
| 72 | 2 CF$_3$COOH | N-(3-chlorobenzyl)-N-(4-fluorophenyl)-4-piperidinamine | 319 |
| 73 | 2 HCl, 0.5 H$_2$O | N-(3,4-difluorobenzyl)-N-(4-fluorophenyl)-4-piperidinamine | 321 |
| 74 | 2 CF$_3$COOH | N-(3,4-difluorobenzyl)-N-(4-fluorophenyl)-4-piperidinamine | 321 |
| 75 | 2 HCl, 0.5 H$_2$O | N-(4-fluorobenzyl)-N-(4-fluorophenyl)-4-piperidinamine | 303 |
| 76 | 2 CF$_3$COOH | N-(4-fluorobenzyl)-N-(4-fluorophenyl)-4-piperidinamine | 303 |
| 77 | 2 HCl | N-(4-fluorobenzyl)-N-(4-fluorophenyl)-4-piperidinamine | 303 |
| 78 | 2 HCl, 0.5 H$_2$O | N-(4-chlorobenzyl)-N-(4-fluorophenyl)-4-piperidinamine | 319 |
| 79 | 2 CF$_3$COOH | N-(4-chlorobenzyl)-N-(4-fluorophenyl)-4-piperidinamine | 319 |
| 80 | 2 CF$_3$COOH | N-(3,4-dichlorobenzyl)-N-(4-fluorophenyl)-4-piperidinamine | 353/355/357 |
| 81 | 2 HCl, 1 H$_2$O | N-(4-fluorophenyl)-N-(4-methylbenzyl)-4-piperidinamine | 299 |
| 82 | 2 CF$_3$COOH | N-(4-fluorophenyl)-N-(4-methylbenzyl)-4-piperidinamine | 299 |
| 83 | 2 HCl, 0.5 H$_2$O | N-(4-fluorophenyl)-N-[4-(trifluoromethyl)benzyl]-4-piperidinamine | 353 |
| 84 | 2 HCl | N-(4-fluorophenyl)-N-[4-(trifluoromethyl)benzyl]-4-piperidinamine | 353 |
| 85 |  | N-(4-chlorophenyl)-N-(4-fluorobenzyl)-4-piperidinamine | 319 |
| 86 | 2 CF$_3$COOH | N-(3-chlorobenzyl)-N-(4-methylphenyl)-4-piperidinamine | 315/317 |
| 87 | 2 CF$_3$COOH | N-(3,4-difluorobenzyl)-N-(4-methylphenyl)-4-piperidinamine | 317 |
| 88 | 2 CF$_3$COOH | N-(4-fluorobenzyl)-N-(4-methylphenyl)-4-piperidinamine | 299 |
| 89 | 2 CF$_3$COOH | N-(4-chlorobenzyl)-N-(4-methylphenyl)-4-piperidinamine | 315/317 |
| 90 | 2 CF$_3$COOH | N-(3,4-dichlorobenzyl)-N-(4-methylphenyl)-4-piperidinamine | 349/351/353 |
| 91 | 2 CF$_3$COOH | N-(4-methylphenyl)-N-[4-(trifluoromethyl)benzyl]-4-piperidinamine | 349 |
| 92 |  | N-(4-fluorobenzyl)-N-[4-(trifluoromethyl)phenyl]-4-piperidinamine | 353 |

EXAMPLE 2

Binding Assays 2.1 H1 Binding

Affinity of the test compounds for the human histamine H1 receptor was evaluated by a [$^3$H]-mepyramine binding assay. This binding was performed as described by Gillard et al. (Gillard M., Van der Perren C., Moguilevsky N., Massingham R, Chatelain P., Mol. Pharmacol. (2002), 61, 391-399).

2.2 5-HT Uptake

Affinity of the test compounds for the Serotonin Transporter was evaluated by a [$^3$H]-Paroxetine binding assay. This binding was performed as described by Marcusson et al. (Marcusson J. O., Bergstrom M., Eriksson K., Ross S. B., J. Neurochem. (1988), 50, 1783) with slight modifications.

Membrane proteins (100-200 μ) from rat cerebral cortex were incubated for 120 min at 25° C. in 2 ml of a 50 mM Tis-HCl (pH 7.4) buffer containing 2 mM MgC12 and 0.05 nM radioligand. Non specific binding defined as the residual binding was measured in the presence of 5 μM Imipramine.

2.3 5-HT2 Binding

The affinity of the test compounds for the 5-HT2 receptors was evaluated by a [$^3$H]-Ketanserine binding assay. This binding was performed according to Leysen et al. (Leysen J. E., Niemegeers C. J., Van Nueten J. M., Laduron P. M., Mol. Pharmacol. (1982), 21, 301-314) with slight modifications. Briefly, 250 μg of membrane proteins from rat cerebral cortex were incubated for 60 min at 25° C. in 1 ml of a 50 mM Tris-HCl (pH 7.4) buffer containing 2 mM MgCl$_2$ and 0.2 nM radioligand. Non specific binding was defined as the residual binding measured in the presence of 1 μM Chlorpromazine.

The invention claimed is:

1. A 4-aminopiperidine compound of formula I or a pharmaceutically acceptable salt thereof,

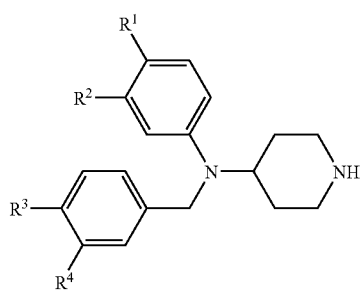

(I)

wherein $R^1$, $R^2$, $R^3$, $R^4$ independently are selected from hydrogen, fluorine, chlorine, methyl and trifluoromethyl, with the proviso that, if $R^1$ $R^2$ and $R^4$ are hydrogen, then $R^3$ is not hydrogen, fluorine, or chlorine.

2. A 4-aminopiperidine compound according to claim 1 wherein $R^2$ is hydrogen, fluorine or methyl, and $R^4$ is hydrogen, fluorine, chlorine or trifluoromethyl.

3. A 4-aminopiperidine compound according to claim 1 wherein $R^1$ is hydrogen, fluorine or chlorine; $R^2$ is hydrogen, fluorine or methyl; $R^3$ is hydrogen, fluorine, chlorine or methyl; and $R^4$ is hydrogen, fluorine or chlorine.

4. A 4-aminopiperidine compound according to claim 1 wherein $R^1$ is hydrogen or fluorine; $R^2$ is hydrogen or fluorine; $R^3$ is fluorine or methyl: and $R^4$ is hydrogen.

5. A 4-aminopiperidine compound according to claim 1 selected from the group consisting of
N-(4-methylbenzyl)-N-phenyl -4-piperidinamine;
N-(4-fluorobenzyl)-N-(3-fluorophenyl)-4-piperidinamine;
N-(3 -fluorophenyl)-N-(4-methylbenzyl)-4-piperidinamine;
N-(4-fluorobenzyl)-N-(4-fluorophenyl)-4-piperidinamine;
N-(4-fluorophenyl)-N-(4-methylbenzyl)-4-piperidinamine; or a pharmaceutically acceptable salt thereof.

6. N-(4-fluorobenzyl)-N-(3-fluorophenyl)-4-piperidinamine or a pharmaceutically acceptable salt thereof.

7. N-(3 -fluorophenyl)-N-(4-methylbenzyl)-4-piperidinamine or a pharmaceutically acceptable salt thereof.

8. A pharmaceutical composition comprising as active ingredient a therapeutically effective amount of a compound according to claim 1 and a pharmaceutically acceptable adjuvant, diluent or carrier.

9. A compound of formula II,

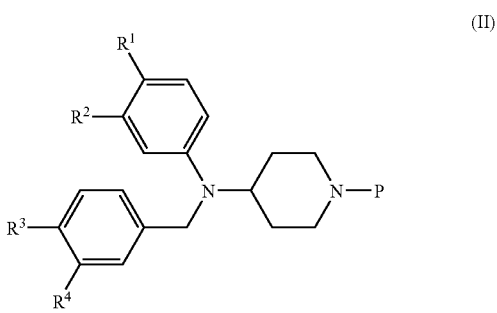

(II)

wherein $R^1$, $R^2$, $R^3$, $R^4$ independently are selected from hydrogen, fluorine, chlorine, methyl and trifluoromethyl with the proviso that, if $R^1$, $R^2$ and $R^4$ are hydrogen, then $R^3$ is not hydrogen, fluorine, or chlorine; and P is,-methoxycarbonyl, ethoxycarbonyl, tert-butoxycarbonyl, 9-fluorenylmethoxycarbonyl, 9-(2-sulfo)fluorenylmethoxycarbonyl, 9-(2,7-dibromo)fluorenylmethoxycarbonyl, 2,2,2-trichloroethoxycarbonyl, 2-phenylethoxycarbonyl, 2-chloroethoxycarbonyl, benzyloxycarbonyl, p-methoxybenzyloxycarbonyl, benzenesulfenyl, 2-nitrobenzenesulfenyl, tosyl, benzenesulfonyl, methyl, tert-butyl, allyl, benzyl, bis(4-methoxyphenyl)methyl or 2,4-dinitrophenyl.

10. The compound according to claim 9 selected from the group consisting of
tert-butyl 4-[3-fluoro(4-fluorobenzyl]anilino]-1-piperidinecarboxylate;
tert-butyl 4-{[3-(trifluoromethyl)benzyl]aniline}-1-piperidinecarboxylate;
tert-butyl 4-{(3-chlorobenzyl)aniline]-1-pipendinecarboxylate;
tert-butyl 4-[(3,4-difluorobenzyl)aniline]-1-piperidinecarboxylate;
tert-butyl 4-[(3,4-dichlorobenzyl)anilinoI]-1-piperidinecarboxylate;
tert-butyl 4-[(3,4-methylbenzyl)anilino)-1-piperidinecarboxylate;
tert-butyl 4-{[4-(trifluoromethyl)benzyl]aniline }-1-piperidinecarboxylate;
tert-butyl 4-[(3 ,4-difluorobenzyl)-3-fluoroanilino]-1-piperidinecarboxyiate;
tert-butyl 4-[(4-chlorobenzyl)-3-fluoroanilino]-1-piperidinecarboxylate;
tert-butyl 4-[(3 ,4-dichlorobenzyl)-3-fluoroanilino]- 1-piperidinecarboxylate;
tert-butyl 4-{3 -fluoro(4-methylbenzyl)anilno]-1-piperidinecarboxylate;
tert-butyl 4-{3-fluoro [4(trifluoromethyl)benzyl]aniline }-1-piperidinecarboxylate;
tert-butyl 4-[(3-chlorobenzyl)-3-methylanilino]-1-piperidinecarboxylate;
tert-butyl 4-[(3 ,4-difluorobenzyl)-3-methylanilino]- 1-piperidinecarboxylate;
tert-butyl 4-[(4-fluorobenzyl)-3-methylanilino]-1-piperidinecarboxylate;
tert-butyl 4-[(4-chlorobenzyl)-3-methylanilino]- 1-piperidinecarboxylate;

tert-butyl 4-[(3,4-dichlorobenzyl)-3-methylanilino]-1-piperidinecarboxylate;

tert-butyl 4-(3-methy[4-(trifluoromethyl)benzyl]aniline)-1-piperidinecarboxylate;

tert-butyl 4-(benzyl-4-fluoroanilino)-1-piperidinecarboxylate;

tert-butyl 4-{4-fluoro [3(trifluoromethyl)benzyl]aniline}-1-piperidinecarboxylate;

tert-butyl 4-[(3-chlorobenzyl)-4-fluoroanilino]-1-piperidinecarboxylate;

tert-butyl 4-[(3,4-difluorobenzyl)-4-fluoroanilino]-1-piperidinecarboxylate;

tert-butyl 4-[4-fluoro(4-fluorobenzyl)aniline]-1-piperidinecarboxylate;

tert-butyl 4-[(4-chlorobenzyl)-4-fluoroanilino]-1-piperidinecarboxylate;

tert-butyl 4-[(3,4-dichlorobenzyl)-4-fluoroanilino]-1-piperidinecarboxylate;

tert-butyl 4-[4-fluoro(4-methylbenzyl)aniline]-1-piperidinecarboxylate;

tert-butyl 4-{4-fluoro [4-(trifluoromethyl)benzyl]anilino]-1-piperidinecarboxylate;

tert-butyl 4- [4-chloro(4-fluorobenzyl)anilino]-1-piperidinecarboxylate;

tert-butyl 4-[(3-chlorobenzyl)-4-methylanilino]-1-piperidinecarboxylate;

tert-butyl 4-[(3,4difluorobenzyl)-4-methlyanilino]-1-piperidinecarboxylate;

tert-butyl 4-[(4-fluorobenzyl)-4-methylanilino]-1-piperidinecarboxylate;

tert-butyl 4-[(4-chlorobenzyl)-4-methylanilino]-1-piperidinecarboxylate;

tert-butyl 4-[(3,4-dichlorobenzyl)-4-methylanilino]-1-piperidinecarboxylate;

tert-butyl {4[4-methyl(4-trifluoromethyl)benzyl]aniline}-1-piperidinecarboxylate;

tert-butyl 4-[(4-fluorobenzyl)-4-(trifluoromethyl)aniline]-1-piperidinecarboxylate; and tert-butyl 4-[(3-chlorobenzyl)-3-fluoroanilino]-1-piperidinecarboxylate.

\* \* \* \* \*